United States Patent [19]

Le Pennec et al.

[11] 4,398,049
[45] Aug. 9, 1983

[54] OLIGOMERIZATION CATALYST AND PROCESS

[75] Inventors: Dominique Le Pennec, Trappes; Dominique Commereuc, Meudon; Yves Chauvin, Le Pecq, all of France

[73] Assignee: Institut Francais du Petrole, Rueil-Malmaison, France

[21] Appl. No.: 425,347

[22] Filed: Sep. 28, 1982

Related U.S. Application Data

[60] Division of Ser. No. 248,582, Mar. 27, 1981, Pat. No. 4,366,067, which is a continuation-in-part of Ser. No. 183,792, Sep. 3, 1980, Pat. No. 4,316,851.

[30] Foreign Application Priority Data

Sep. 3, 1979 [FR] France .............................. 79 22153

[51] Int. Cl.$^3$ .......................... C07C 3/12; C07C 3/18; C07C 3/21
[52] U.S. Cl. .................................. 585/512; 585/531; 252/431 C; 526/119; 526/118
[58] Field of Search ....................... 585/510, 512, 531; 526/118, 119, 110, 112; 252/431 C, 442

[56] References Cited

U.S. PATENT DOCUMENTS

| | | | |
|---|---|---|---|
| 3,655,810 | 4/1972 | Orsay et al. | 585/512 |
| 4,225,743 | 9/1980 | Hoshiyama et al. | 585/512 |
| 4,283,305 | 8/1981 | Chauvin et al. | 585/512 |
| 4,357,478 | 11/1982 | Hillion et al. | 252/431 C |
| 4,362,650 | 12/1982 | Chauvin et al. | 585/512 |
| 4,366,087 | 12/1982 | La Pennec et al. | 252/431 C |

FOREIGN PATENT DOCUMENTS

| | | | |
|---|---|---|---|
| 41-77168 | 11/1966 | Japan | 585/512 |
| 53-78949 | 6/1978 | Japan | 585/512 |
| 2045797 | 11/1980 | United Kingdom | 585/512 |

*Primary Examiner*—Delbert E. Gantz
*Assistant Examiner*—A. Pal
*Attorney, Agent, or Firm*—Millen & White

[57] ABSTRACT

A catalyst composition is manufactured by admixing a hydrocarbyl aluminum halide of a nickel compound of the formula $(R_1COO)(R_2COO)Ni$, where $R_1$ is hydrocarbyl with at least 5 carbon atoms and $R_2$ is haloalkyl of 1–3 carbon atoms. Olefins such as ethylene, propylene and butenes can be oligomerized, for example, dimerized and trimerized, with the above catalyst composition.

11 Claims, 5 Drawing Figures

OLIGOMERIZATION CATALYST AND PROCESS

The present application is a divisional application of our prior application Ser. No. 06/248,582, filed Mar. 27, 1981, now U.S. Pat. No. 4,366,067, which is in turn a continuation-in-part of our prior application Ser. No. 183,792, filed Sept. 3, 1980, now U.S. Pat. No. 4,316,851.

BACKGROUND OF THE INVENTION

Bivalent nickel inorganic salts are well-known. They are usually soluble in aqueous medium and have little solubility, if any, in hydrocarbon medium. Conversely, bivalent nickel salts of carboxylic acids of the formula (RCOO)$_2$Ni, where R is a substituted or unsubstituted hydrocarbyl radical, are usually soluble, sometimes in large amount, in the hydrocarbon media, provided the radical R has a sufficient number of carbon atoms. This property is often desired when the nickel salts must be used as homogeneous catalysts, either alone or associated with Lewis acids, such as alkylaluminum compounds. It is true that the use of insoluble nickel salts as catalysts has several known disadvantages, particularly a weaker activity as compared with soluble salts and difficulties of use, particularly in continuous industrial operations where precise and particularly low proportions of catalyst must be used. This explains why it has already been proposed to prepare soluble oligomerization catalysts, such as catalysts for dimerizing or co-dimerizing mono-olefins, by reacting nickel carboxylates with hydrocarbyl aluminum halides.

The use of these catalysts has however the disadvantage that the activity observed in continuous operations is often lower than in batch operations, and even tends to decrease in the course of time. No satisfactory explanation of this phenomenon has yet been found.

OBJECTS OF THE INVENTION

One object of the present invention is to provide a catalyst comprising mixed nickel compounds, soluble in hydrocarbon medium, and hydrocarbyl aluminum halides which have increased catalytic activity and stability, in oligomerization operations particularly as concerns continuous operations. This activity is even higher than that obtained by the combined use of a nickel carboxylate, a halogenoacetic acid and a hydrocarbyl aluminum halide, as disclosed in U.S. Ser. No. 102,488, now U.S. Pat. No. 4,283,305. This new catalyst is useful as catalyst for diolefin polymerization.

DETAILED DISCUSSION

The mixed nickel compound component of the catalyst has the general formula (R$_1$COO) (R$_2$COO)Ni, where R$_1$ is a hydrocarbyl radical, for example an alkyl, cycloalkyl, alkenyl, aryl, aralkyl or alkaryl radical, containing at least 5 carbon atoms, preferably a hydrocarbyl radical of 5–20 carbon atoms, which radical may be substituted with, for example, hydroxy groups, and R$_2$ is a halogenoalkyl radical containing from 1 to 3 carbon atoms, of the formula C$_m$H$_p$X$_q$, where m is 1, 2 or 3, p is zero or an integer and q is an integer, provided that p+q=2m+1. R$_2$ is preferably a halogenomethyl radical CX$_n$H$_{3-n}$ where X is fluorine, chlorine, bromine or iodine and n is an integer from 1 to 3.

The high activity of the catalytic compositions obtained from the above nickel compounds and hydrocarbyl aluminum halides is the more unexpected as the catalytic compositions obtained from nickel bis (halogenoacetates) and hydrocarbyl aluminum halides have a relatively poor activity, probably due to the insolubility of these nickel compounds in hydrocarbon media. The new nickel compounds according to the invention have conversely a substantial solubility in hydrocarbon media, i.e. a solubility of at least 0.1 g per liter in the conditions of use.

The mixed compounds (R$_1$COO) (R$_2$COO)Ni may be manufactured by reacting the mixture of the two acids R$_1$COCH and R$_2$COOH in substantially equimolecular quantities with nickel metal or a nickel oxide, hydroxide or carbonate. They can also be prepared in aqueous medium by contacting water-soluble alkali metal salts (including ammonium salts) of the two acids R$_1$COOH and R$_2$COOH in proportions which are preferably substantially equimolecular, with a bivalent nickel salt soluble in water. Examples of useful salts are nickel chloride, nickel bromide, nickel iodide, nickel sulfate and nickel nitrate and their hydrates. The alkali metal salts may be formed in situ by using organic acids and operating in the presence of a base providing the alkali metal.

The reaction is preferably effected in a liquid biphasic medium comprising an aqueous phase and a substantially immiscible organic phase, consisting of aliphatic, cycloaliphatic or aromatic hydrocarbons or mixtures thereof, or of halogenated hydrocarbons, for example, chlorinated, fluorinated or brominated hydrocarbons. Use may be made of, for example, pentane, heptane, petroleum ether, naphtha, cyclohexane, toluene, xylenes, ethylbenzene, methylene chloride or chloroform. The aqueous phase and the alkali metal salt formed by double decomposition are separated thereafter.

According to another operating procedure, the mixture of the alkali metal salts of the two acids R$_1$COOH and R$_2$COOH may be prepared in a lower alcohol having, for example, 1 to 4 carbon atoms, for example, methanol or ethanol, and the nickel salt is added thereafter. After reaction, the alcohol is removed at least in major part, by distillation and is replaced with a hydrocarbon or a halogenated hydrocarbon as above described. The inorganic salts can then be eliminated by filtration.

According to a modified embodiment, the mixture of the alkali metal salts of the two acids R$_1$COOH and R$_2$COOH may be prepared in a mixed medium comprising an alcohol, for example methanol or ethanol, and a hydrocarbon or a halogenated hydrocarbon as above described. The composition of the alcohol-hydrocarbon mixture may be selected at will; for example, the mixture may have the same composition as the azeotrope, if any, formed by the two solvents. The alcohol or solvent mixture can be removed thereafter.

Another operating procedure, which also leads to the mixed compounds (R$_1$COO) (R$_2$COO)Ni, consists of separately preparing, according to known methods, the two compounds (R$_1$COO)$_2$Ni and (R$_2$COO)$_2$Ni and then reacting these two compounds in substantially equimolecular proportions in a liquid medium comprising a polar solvent, for example, water or an alcohol, and a non-polar solvent, for example a hydrocarbon or a halogenated hydrocarbon, and subsequently eliminating the polar solvent by distillation.

When using free acids as starting compounds, the base providing the alkali metal is preferably used in substantially stoichiometrical amount with respect to the two acids in the form of, for example, sodium or potassium hydroxide, or the corresponding carbonates or hydrogenocarbonates, or ammonia.

It may however be advantageous, in order to facilitate the isolation of the nickel salt, to operate with a slight insufficiency, for example of 5–30%, with respect to the stoichiometry, of one of the reactants, for example an insufficient amount of the base.

The acids or their salts may be used in stoichiometrical proportions with respect to the nickel salt, but different proportions can also be used. Thus an excess of nickel salt, for example a molar excess of 5 to 20%, is favorable to the recovery of a pure product.

The order of supply of the reactants is not critical. However it is preferred to admit first the two acids $R_1COOH$ and $R_2COOH$ with the base in a polar medium, so as to obtain the salts, and then introduce the nickel salt and the hydrocarbon phase.

The proportion of water or alcohol to be used is not critical; however, according to the invention, the best results are obtained with the minimum amount necessary to dissolve the reactants at the reaction temperature. The amount of hydrocarbon phase must be sufficient to dissolve the mixed salt. It then depends on the nature of the reactants; a preferred amount is selected between 2 and 100 times the amount of water or alcohol.

The reaction temperature depends on the reaction facilities; it is however preferred to heat the reaction mixture at reflux under atmospheric pressure, or at a higher or lower pressure, up to stable coloration of the organic phase. This operation may take from 5 minutes to 5 hours, depending on the reflux temperature.

The polar phase, containing the inorganic salts, may be withdrawn by decantation and discharged; it has however been observed, and this is another particular feature of the invention, that particularly high reaction velocities and yields, as concerns the mixed nickel compounds, are obtained by heteroazeotropic distillation of the polar solvent. This distillation is preferably continued up to complete removal of the polar phase. In that case, the resultant inorganic salts are separated by decantation or filtration. The hydrocarbon or halogenated hydrocarbon solvent may be evaporated or distilled and the nickel compound may be isolated as a generally amorphous green solid; for specific uses, however, it can be used as a solution.

Another object of the present invention is to use these mixed bivalent nickel salts as components of a new catalyst composition useful for oligomerizing, and particularly dimerizing and trimerizing mono-olefins. This new composition concerns more precisely the combinations obtained by contacting, in any order, at least one mixed nickel salt with at least one hydrocarbyl aluminum halide.

The following compounds may be used, alone or as mixtures, the list being however not limitative: nickel 2-ethylbutyrate trifluoroacetate, nickel 2-ethylbutyrate trichloroacetate, nickel 3,3-dimethylbutyrate trifluoroacetate, nickel 3,3-dimethylbutyrate trichloroacetate, nickel 4-methylvalerate trifluoroacetate, nickel hexanoate trichloroacetate, nickel heptanoate trifluoroacetate, nickel heptanoate trichloroacetate, nickel heptanoate tribromoacetate, nickel heptanoate triiodoacetate, nickel 2-ethylhexanoate trifluoroacetate, nickel 2-ethylhexanoate monofluoroacetate, nickel 2-ethylhexanoate trichloroacetate, nickel 2-ethylhexanoate dichloroacetate, nickel 2-ethylhexanoate monochloroacetate, nickel 2-ethylhexanoate tribromoacetate, nickel 2-ethylhexanoate triiodoacetate, nickel octoate trifluoroacetate, nickel octoate trichloroacetate, nickel decanoate trifluoroacetate, nickel decanoate trichloroacetate, nickel myristate trifluoroacetate, nickel palmitate trifluoroacetate, nickel dodecylbenzoate trifluoroacetate, nickel diisopropylsalicylate trichloroacetate, nickel myristate pentafluoropropionate and nickel 2-ethylhexanoate heptafluorobutyrate.

Preferred hydrocarbylaluminum halides have the general formula $Al_2R_xY_y$ where R is a hydrocarbon group containing up to 12 carbon atoms, or more, such as alkyl, aryl, aralkyl, alkaryl, cycloalkyl; Y represents halogen: fluorine, chlorine, bromine or iodine; x and y have each a value of 2,3 or 4 with $x+y=6$. Examples of such compounds are ethyl aluminum sesquichloride, dichloroethylaluminum, dichloroisobutylaluminum, chlorodiethylaluminum or their mixtures. Examples of catalyst compositions consist of any one of the mixed nickel compounds of the above list and any one of the aluminum compounds mentioned above.

A preferred catalytic composition consists essentially of at least one nickel compound of the formula $(R_1COO)(R_2COO)Ni$, wherein $R_1$ is alkyl of 5–20 carbon atoms and $R_2$ is trifluoromethyl or trichloromethyl and at least one hydrocarbyl aluminum halide of the formula $Al_2R_xY_y$, wherein R is alkyl of 1–12 carbon atoms, Y is chlorine, x is 2 or 3 and y is 6-x.

Preferably $R_2$ is trifluoromethyl in the above composition.

The invention has also for object a process for oligomerizing mono-olefins in the presence of the above catalytic compositions at a temperature of $-20°$ C. to $+80°$ C. at pressure conditions such that the reactants are maintained, at least in major part, in liquid or condensed phase.

Mono-olefins which can be dimerized or oligomerized are, for example, ethylene, propylene, n-butenes, n-pentenes, either pure or as mixtures such as recovered from synthesis processes, for example, catalytic cracking or steam-cracking. They can be co-oligomerized either together or with isobutene, for example, ethylene with propylene and n-butenes, propylene with n-butenes or n-butenes with iso-butene.

The concentration, expressed as nickel, of the catalytic composition in the liquid phase of the oligomerization reaction, is normally comprised between 5 and 500 parts per million by weight. The molar ratio of the hydrocarbyl aluminum halide to the nickel compound is normally comprised between 1:1 and 50:1, more advantageously between 2:1 and 20:1.

The process may be operated with separate charges but offers a maximum of advantages when operated continuously. In that case, a reactor with one or several serially arranged reaction stages may be used, the olefinic charge and/or the catalyst constituents being continuously introduced either into the first stage or in the first and any other stage. The second and $n^{th}$ stage may also be fed only with additional amounts of one constituent of the catalytic mixture.

At the outlet of the reactor, the catalyst may be deactivated in known manner, for example, with ammonia and/or an aqueous sodium hydroxide solution and/or an aqueous sulfuric acid solution. The unconverted olefins and the alkanes, if any, are separated thereafter from the oligomers by distillation.

Figure 1:
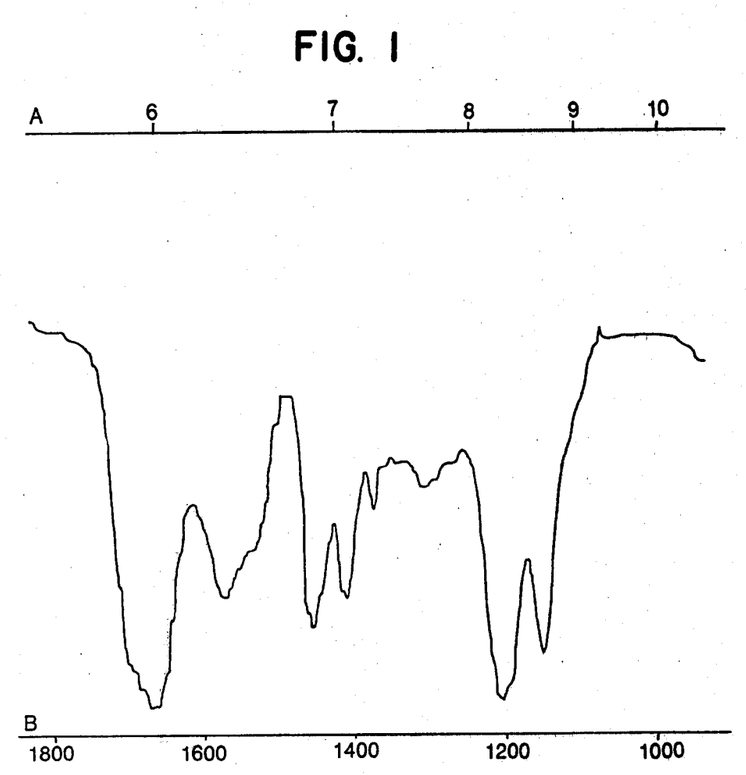
FIGS. 1–5 show the infrared spectra of mixed nickel compounds prepared in Examples 1–5.
Figure 2:
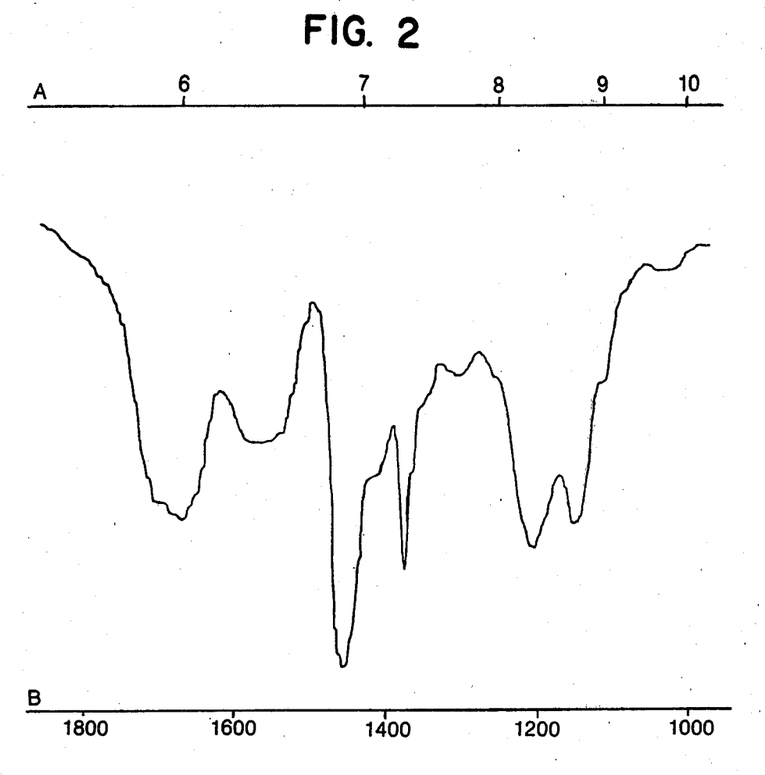
Figure 3:
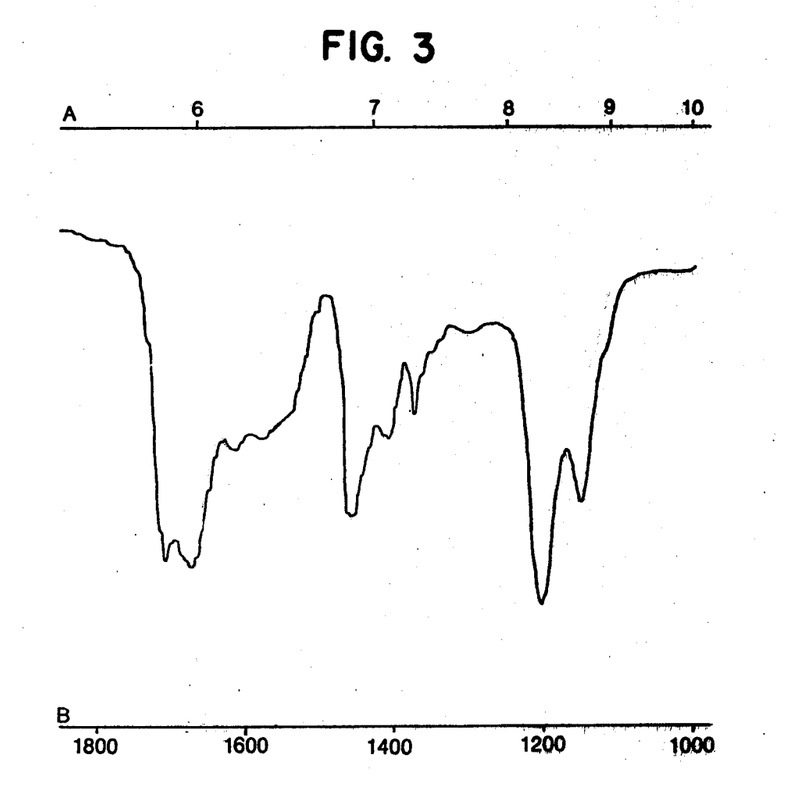
Figure 4:
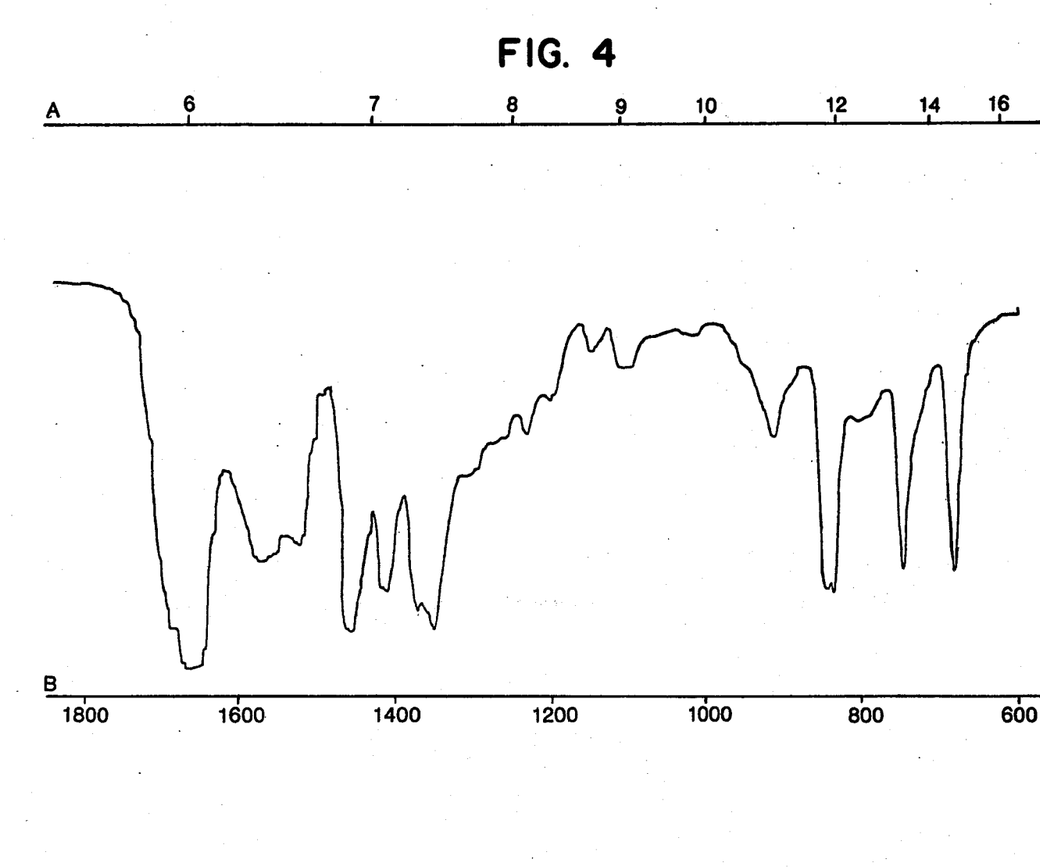
Figure 5:
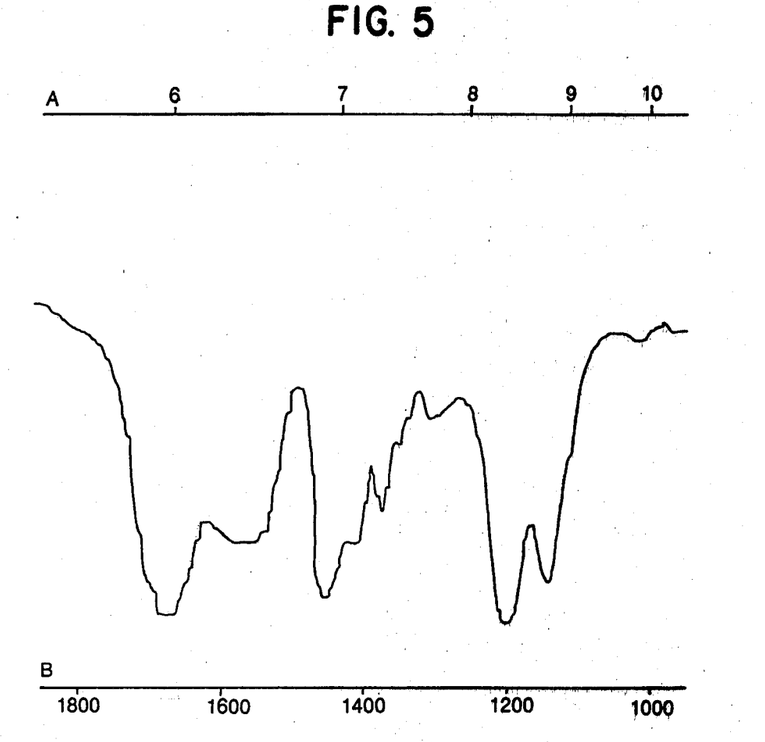

The following examples illustrate the invention but constitute no limitation thereof. The characteristic portion of the infra-red absorption spectrum of the compounds obtained in examples 1 to 5 is shown in FIGS. 1 to 5 (Nujol, KBr). A is the wave length in microns and B the frequency in wave numbers (cm$^{-1}$).

EXAMPLE 1

14.4 g of 2-ethyl hexanoic acid (0.1 mole), 200 cm$^3$ of heptane, 11.4 g of trifluoroacetic acid (0.1 mole), 10.6 g of sodium carbonate, 23.7 g of nickel chloride hexahydrate (0.1 mole) and 25 cm$^3$ of water are successively introduced into a 500 cm$^3$ glass reaction vessel provided with a magnetic stirring rod and a device for heteroazeotropic distillation. The contents are heated to reflux and water is eliminated by azeotropic distillation. An insoluble precipitate containing NaCl is filtered and washed with heptane; the organic phase is evaporated under vacuum. There remains a solid of intense green color, which is identified by elemental analysis and infra-red spectrometry as nickel 2-ethyl hexanoate trifluoroacetate. Elemental analysis: calculated for $C_{10}H_{15}O_4F_3Ni$: C=38.1; H=4.8; Ni=18.7; found (%): C=38.7; H=5.6; Ni=16.9. Infra-red spectrum: characteristic bands at 1670 cm$^{-1}$ ($CF_3COO$), 1575 and 1410 cm$^{-1}$ ($C_7H_{15}COO$), 1205 and 1150 cm$^{-1}$ ($CF_3$). 29.5 g of the mixed salt have been obtained, corresponding to a yield of 93.1%.

It has been proved that the above salt is a mixed compound and not a mixture of nickel trifluoroacetate with nickel 2-ethyl hexanoate: nickel trifluoroacetate is insoluble in hydrocarbons; if formed, it would have been eliminated in the solid state and the yield of hydrocarbon-soluble compound would have been far lower.

EXAMPLE 2

The operation is conducted as in example 1, while successively introducing: 80 cm$^3$ of heptane, 5 cm$^3$ of water, 0.91 g of trifluoroacetic acid (8×10$^{-3}$ mole), 1.04 g of heptanoic acid (8×10$^{-3}$ mole), 0.64 g of sodium hydroxide (1.6×10$^{-2}$ mole) and finally 2.81 g of nickel sulfate heptahydrate (10$^{-2}$ mole). A green solid is obtained (weight: 2.23 g; yield: 88.8%) identified as being nickel heptanoate trifluoroacetate. Elemental analysis: calculated for $C_9H_{13}O_4F_3Ni$: C=35.9; H=4.3; F=18.9; Ni=19.6; found (%) C=35.6; H=4.5; F=18.7; Ni=19.1. Infra-red spectrum: characteristic bands at 1675 cm$^{-1}$ ($CF_3COO$), 1570 cm$^{-1}$ ($C_6H_{13}COO$), 1205 and 1150 cm$^{-1}$ ($CF_3$).

EXAMPLE 3

The operation is conducted as in example 1, while reacting: 80 cm$^3$ of heptane, 5 cm$^3$ of water, 0.91 g trifluoroacetic acid (8×10$^{-3}$ mole), 1.71 g of myristic acid (8×10$^{-3}$ mole), 0.64 g of sodium hydroxide (1.6×10$^{-2}$ mole) and 2.81 g of nickel sulfate heptahydrate (10$^{-2}$ mole). A green solid (2.80 g) is obtained and identified as being nickel myristate trifluoroacetate (yield: 90.9%). Elemental analysis: calculated for $C_{15}H_{25}O_4F_3Ni$: C=46.8; H=6.5; F=14.8; Ni=15.3; found (%) C=47.7; H=7.1; F=14.4; Ni=14.8. Infra-red spectrum: characteristic bands at 1675 cm$^{-1}$ ($CF_3COO$), 1580 and 1410 cm$^{-1}$ ($C_{12}H_{25}COO$), 1205 and 1150 cm$^{-1}$ ($CF_3$).

EXAMPLE 4

The operation is conducted as in example 1, while reacting: 100 cm$^3$ of heptane, 25 cm$^3$ of water, 5.75 g of 2-ethyl hexanoic acid (4×10$^{-2}$ mole), 6.55 g of trichloroacetic acid (4×10$^{-2}$ mole), 3.20 g of sodium hydroxide (8×10$^{-2}$ mole) and 14.05 g of nickel sulfate heptahydrate (5×10$^{-2}$ mole). A green solid is obtained (10.8 g), which is identified as being nickel 2-ethyl hexanoate trichloroacetate (yield: 74.2%). Elemental analysis: calculated for $C_{10}H_{15}O_4Cl_3Ni$: C=32.9; H=4.1; Ni=16.2; found (%) C=37.5; H=5.7; Ni=15.2. Infra-red spectrum: characteristic bands at 1655 cm$^{-1}$ ($CCl_3COO$), 1570 and 1410 cm$^{-1}$ ($C_7H_{15}COO$), 845 and 835 cm$^{-1}$ ($CCl_3$).

EXAMPLE 5

The process is conducted as in example 1, while reacting: 80 cm$^3$ of heptane, 5 cm$^3$ of water, 0.91 g of trifluoroacetic acid (8×10$^{-3}$ mole), 0.93 g of 4-methyl valeric acid (8×10$^{-3}$ mole), 0.64 g of sodium hydroxide (1.6×10$^{-2}$ mole) and then 2.81 g of nickel sulfate heptahydrate (10$^{-2}$ mole). A green solid is obtained (0.6 g) and identified as being nickel 4-methyl valerate trifluoroacetate (yield: 26%). Elemental analysis: calculated for $C_8H_{11}O_4F_3Ni$: C=33.4; H=3.8; Ni=20.5; found (%) C=33.3; H=3.9; Ni=20.1. Infra-red spectrum: characteristic bands at 1675 cm$^{-1}$ ($CF_3COO$), 1570 and 1410 cm$^{-1}$ ($C_5H_{11}COO$), 1200 and 1145 cm$^{-1}$ ($CF_3$).

EXAMPLE 6

Olefin oligomerization is effected in an oligomerization reactor consisting of two serially arranged reaction stages, each consisting of a double-jacket cylindrical steel reactor of a useful volume of 0.25 liter, whose temperature is controlled by circulating water.

The first stage reactor is continuously fed with 98 g/h of a $C_4$ cut whose composition is as follows:

propane: 1.1% b.w.
isobutane: 6.7
n-butane: 23.0
1-butene: 5.2
trans 2-butene: 46.4
cis 2-butene: 17.6

The reactor is also fed with 0.031 g/h of nickel 2-ethyl hexanoate trifluoroacetate prepared as in example 1, as a solution in heptane, and 0.194 g/h of dichloroethylaluminum as a solution in heptane. A pressure of 5 bars is maintained in the reactors by continuously discharging the reaction product, and the temperature is maintained at 42° C. by means of circulating water.

After 4 hours of run, a steady state run is obtained, corresponding to a 66% conversion of the butenes to oligomers in the first stage and 75% at the outlet of the second stage. The oligomers comprise 85% dimers (n-octenes, methylheptenes and dimethylhexenes), 12% trimers and 3% tetramers. The oligomer yield in this example as well as in the following examples 7, 8 and 10-16 is practically 100% with respect to the converted olefin.

The activity of the catalyst system, expressed as the velocity constant k (mol$^{-1}$.l.h$^{-1}$) defined by the relation V=kC$^2$, where V is the reaction velocity (mol.l$^{-1}$.h$^{-1}$) and C the butenes stationary concentration (mol.l$^{-1}$) in the stages, is:

k (first stage): 0.423 mol$^{-1}$.l.h$^{-1}$
k (second stage): 0.106 mol$^{-1}$.l.h$^{-1}$

EXAMPLE 7

The apparatus is the same as in example 6 and it is continuously fed with 83 g/h of the same $C_4$ cut, 0.036 g/h of nickel 2-ethyl hexanoate trichloroacetate prepared as in example 4 in the form of a solution in heptane, and 0.194 g/h of dichloroethylaluminum as a solution in heptane.

After 4 hours of run, a steady state operating rate is attained, corresponding to a butenes conversion of 64% in the first stage and 77% at the outlet of the second stage. The oligomers analyze substantially as in example 6.

The activity of the catalyst system, expressed as in example 6, is:

k (first stage): $0.307 \text{ mol}^{-1}.\text{l}.\text{h}^{-1}$
k (second stage): $0.152 \text{ mol}^{-1}.\text{l}.\text{h}^{-1}$

COMPARATIVE EXAMPLE 8

This example is given by way of comparison for showing the advantages of the invention.

The apparatus is the same as in example 6. It is continuously fed with 82 g/h of the same $C_4$ cut, 0.052 g/h of a nickel carboxylate having a 11% b.w. nickel content, admixed with 0.011 g/h of trifluoroacetic acid in heptane, and 0.194 g/h of dichloroethylaluminum as a solution in heptane.

The amount of nickel, expressed in g/h of Ni metal, is thus identical to that used in example 6, which permits a direct comparison of the results by means of the constant k.

The state operating rate attained after 4 hours of run corresponds to a 57% conversion in the first stage and 68% at the outlet of the second stage. The activity of the catalyst system is thus substantially lower then in example 6:

k (first stage): $0.193 \text{ mol}^{-1}.\text{l}.\text{h}^{-1}$
k (second stage): $0.067 \text{ mol}^{-1}.\text{l}.\text{h}^{-1}$ The oligomers composition is substantially as in example 6.

EXAMPLE 9

14.4 g of 2-ethyl hexanoic acid (0.1 mole), 100 cm$^3$ of methanol, 11.4 g of trifluoroacetic acid (0.1 mole) and 8.0 g of sodium hydroxide (0.2 mole) are successively fed into a 500 cm$^3$ glass reaction vessel provided with a magnetic stirring rod and a reflux device. The mixture is heated to reflux and 35.1 g (0.125 mole) of nickel sulfate heptahydrate is added. The mixture is heated again at reflux. Methanol is evaporated by means of a rotative evaporator and the residue is taken up in toluene. After filtration of the insoluble inorganic salts, toluene is distilled off and nickel 2-ethyl hexanoate trifluoroacetate is obtained. Its analysis corresponds to the formula $C_{10}H_{15}O_4F_3Ni$ and it has the same characteristic bands as the product of example 1.

EXAMPLE 10

An oligomerization reactor of 35 liter useful volume is continuously fed with 5 kg/h of a $C_3$ cut having the following composition:
propane: 20% b.w.
propylene: 80% b.w.

0.273 g/h of nickel 2-ethyl hexanoate trifluoroacetate as a solution in isooctane and 1.65 g/h dichloroethylaluminum as a solution in isooctane are added. A pressure of 15 bars is maintained by withdrawal of reaction product and a temperature of 42° C. by water circulation. The conversion of propylene to oligomers at steady state running conditions amounts to 90% and the resultant oligomers comprise 85% of dimers (n-hexenes, methylpentenes and dimethylbutenes), 12% of trimers and 3% of tetramers.

EXAMPLE 11

25 g of NiO, 46 cm$^3$ of trifluoroacetic acid and 90 cm$^3$ of distilled water are introduced into a 1-liter glass reaction flask provided with a magnetic stirring rod and a distillation device. The mixture is heated at reflux for 2 hours; then the excess of NiO is filtered. An aqueous solution of nickel trifluoroacetate $Ni(CF_3COO)_2$ is thus obtained in quantitative yield. 135 g of nickel 2-ethyl hexanoate (13% b.w. nickel content) of technical grade, containing 10% of free 2-ethyl hexanoic acid, dissolved in 500 cm$^3$ heptane, are added. After heating at reflux, water is removed by azeotropic distillation. After complete water removal, heptane is separated by evaporation under vacuum. Nickel 2-ethyl hexanoate trifluoroacetate is thus obtained with a yield of 98%. Elemental analysis: calculated for $C_{10}H_{15}O_4F_3Ni$: C=38.1; H=4.8; Ni=18.7; found: C=38.4; H=5.4; Ni=17.8. The infra-red spectrum shows the expected characteristic bands identical to those of example 1.

The above nickel compound has been used to prepare an oligomerization catalyts and to oligomerize a $C_4$ cut under the same conditions as in example 6.

The conversion was 66% in the first stage and 75% at the outlet of the second stage and the oligomers analyzed substantially as in example 6.

EXAMPLES 12-15

The same apparatus as in example 6 is continuously fed with 98 g/h of the same $C_4$ cut and various amounts of a nickel compound and an aluminum compound as stated in Table 1, each of which is used in heptane solution. The reactor pressure is 5 bars and the temperature 42° C.

After 4 h, a steady state run is obtained. The activity of the catalytic system, expressed as in example 6 is also given in Table 1.

EXAMPLE 16

50 g/h of a $C_2$-$C_3$ cut comprising:
ethane: 4.6% b.w.
ethylene: 78.8% b.w.
propylene: 16.6% b.w., 0.016 g/h of nickel 2-ethyl hexanoate trifluoroacetate as a solution in iso-octane and 0.096 g/h of dichloroethylaluminum as a solution in iso-octane are introduced into a 0.25 liter stainless steel reactor.

The temperature is maintained at 42° C. and the pressure at 20 bars by discharge of the reaction product.

After 4 hours, a steady state run is obtained, corresponding to an ethylene conversion of 99.4% and a propylene conversion of 96%. The oligomers yield is quantitative and the oligomers analyze as follows
butenes: 18.9% b.w.
iso-pentenes: 7.4% b.w.
iso-hexenes: 22.6% b.w.
iso-heptenes: 12.7% b.w.
iso-octenes: 12.5% b.w.
higher olefins: 25.9% b.w.

Other specific examples of catalytic compositions are (molar proportions):
nickel decanoate dichloracetate + dichloroethyl aluminium (6:1)

nickel stearate monofluoracetate+ethyl aluminum sesquichloride (4:1)

nickel 4-methylvalerate tribromoacetate+dichloroethylaluminum (4.5:1)

nickel octoate trifluoracetate+monochlorodiisobutyl aluminum (8:1)

These compositions can be used successfully under the conditions of example 6.

TABLE 1

| Example | Ni compound | Feed rate of the Ni compound | Al compound | Feed rate of the Al compound | Catalytic activity k (1st stage) mol$^{-1}$.l.h$^{-1}$ | k (2nd stage) mol$^{-}$.l.h$^{-1}$ |
|---|---|---|---|---|---|---|
| 12 | 2-ethyl-hexanoate trifluoroacetate | 0,031 | Al$_2$Et$_3$Cl$_3$ | 0,189 | 0,390 | 0,110 |
| 13 | Myristate trifluoroacetate | 0,038 | Al Et Cl$_2$ | 0,194 | 0,350 | 0,100 |
| 14 | 4-ethyl-valerate trifluoroacetate | 0,028 | Al Et Cl$_2$ | 0,194 | 0,325 | 0,105 |
| 15 | 2-ethyl-hexanoate trifluoroacetate | 0,031 | Al(i-C$_4$H$_9$)Cl$_2$ | 0,237 | 0,405 | 0,115 |

To summarize, mixed nickel salts used as a component of the catalyst of the invention may be prepared by reacting a source of R$_1$COO- ion in solution with a source of R$_2$COO- ion in solution and a source of nickel ion (which may be common with the two above sources) in solution. The solvent used for the dissolution may be common to all the sources or distinct solvents may be used. A polar solvent, preferably water and/or an alcohol, is commonly used. Simultaneously, or subsequently, a hydrocarbon solvent or a halogenated hydrocarbon solvent is added and the polar solvent is removed, preferably by distillation. The mixed salt is obtained as a solution in the hydrocarbon or the halogenated hydrocarbon.

What is claimed is:

1. A process of oligomerizing C$_{1-5}$ monoolefins, comprising contacting the olefins with a catalyst composition consisting essentially of at least one hydrocarbyl aluminum halide and at least one nickel compound having the formula (R$_1$COO) (R$_2$COO)Ni, wherein R$_1$ is a hydroxy-substituted or unsubstituted C$_{5-20}$ hydrocarbyl radical; and R$_2$ is a haloalkyl group having the formula C$_m$H$_p$X$_q$, wherein m is 1,2 or 3 p is zero or an integer; q is an integer; and p+q=2m+1; the molar ratio of the hydrocarbyl aluminum halide to the nickel compound being from 1:1 to 50:1, said contacting being effected at a temperature of −20° C. to 80° C. and a pressure sufficient to maintain the olefins in the liquid or condensed phase, at least in major part.

2. A process according to claim 1, wherein the amount of the catalyst composition in the liquid phase of the oligomerization reaction, expressed as nickel, is 5-500 ppm by weight.

3. A process according to claim 1, wherein R$_1$ is C$_{5-20}$ alkyl, and R$_2$ is trifluoromethyl or trichloromethyl.

4. A process according to claim 1, wherein the hydrocarbyl aluminum halide has the formula Al$_2$R$_x$Y$_y$, wherein R is C$_{1-12}$ hydrocarbyl; Y is halogen; x and y are each 2, 3 or 4; and X+y=6; and wherein the molar ratio of the hydrocarbyl aluminum halide to the nickel compound is from 2:1 to 20:1.

5. A process according to claim 4, wherein R is C$_{1-12}$ alkyl; Y is chlorine, x is 3; and y is 3.

6. A process according to claim 4, wherein R is C$_{1-12}$ alkyl; Y is chlorine; x is 2; and y is 4.

7. A process according to claim 3, wherein the hydrocarbyl aluminum halide has the formula Al$_2$R$_x$Y$_y$; wherein R is C$_{1-12}$ alkyl; Y is chlorine; x is 2 or 3; and y is 6-x.

8. A process according to claim 3, wherein the hydrocarbyl aluminum halide has the formula Al$_2$R$_x$Y$_y$, wherein R is C$_{1-12}$ alkyl; Y is chlorine; x is 2; and y is 4.

9. A process according to claim 7, wherein R$_2$ of the nickel compound is trifluoromethyl.

10. A process according to claim 3, wherein R$_1$COO in said nickel compound is 2-ethylhexanoate, heptanoate, myristate, 4-methylvalerate, decanoate or octoate.

11. A process according to claim 1, wherein the hydrocarbyl aluminum halide is ethyl aluminum sesquichloride, dichloroethylaluminum, dichloroisobutylaluminum, chlorodiethylaluminum, chlorodiisobutylaluminum, or mixtures thereof.

* * * * *